United States Patent [19]
Usui et al.

[11] Patent Number: 6,128,966
[45] Date of Patent: Oct. 10, 2000

[54] INSPECTION METHOD FOR ENDODONTIC FILES, AND EQUIPMENT FOR SAME

[75] Inventors: Masayoshi Usui; Kazunori Takikawa, both of Numazu, Japan

[73] Assignee: Usui Kokusai Sangyo Kaisha Limited, Japan

[21] Appl. No.: 09/216,991

[22] Filed: Dec. 21, 1998

[30] Foreign Application Priority Data

Dec. 29, 1997 [JP] Japan ................................. 9-369621

[51] Int. Cl.[7] ................................................ G01M 19/00
[52] U.S. Cl. ........................................... 73/865.8; 433/114
[58] Field of Search .................... 73/763, 865.8; 433/114

[56] References Cited

U.S. PATENT DOCUMENTS

| | | | |
|---|---|---|---|
| 4,518,356 | 5/1985 | Green | 433/102 |
| 4,708,651 | 11/1987 | Buchanan | 433/157 |
| 5,368,482 | 11/1994 | Johnsen et al. | 433/163 |
| 6,036,490 | 3/2000 | Johnsen et al. | 433/102 |

*Primary Examiner*—Max Noori
*Attorney, Agent, or Firm*—Anthony J. Casella; Gerald E. Hespos; Michael J. Porco

[57] ABSTRACT

An inspection equipment is provided by which the endodontic file is examined and judged as to if it reaches to its critical strength. When an appropriately selected endodontic file out of the endodontic files 11, 12, 13 in the kit case 1 is set at the file sample holding portion 5 in the kit case 1 and data corresponding to the endodontic file is input from the data input portion 22, the electric resistance value on the file portion of the endodontic file measured by the resistance measuring portion 20 and the resistance value on the critical strength with correspondence to the data on the file read-out from the RAM 23 are brought together and compared by the inspection unit 30. If the calculating judgement portion 25 makes a judgement to the file to reach its critical level of strength in the cumulative damage, the alarm 19 issues an alarm sound, so that an endodontist or dental assistant knows that the file is not usable any more and should be discarded. As a result, the partially damaged file has no risk to be broken inside the occluded root canal and nickel-associated risk can be eliminated because the partially damaged file can be removed from the continuous service condition according to the present invention. Hence, a safe and reliable endodontic therapy can be practiced.

8 Claims, 3 Drawing Sheets

INSPECTION METHOD FOR ENDODONTIC FILES, AND EQUIPMENT FOR SAME

BACKGROUND OF THE INVENTION

1. Field of the Invention

The present invention relates generally to the endodontics. More particularly, the invention relates to novel inspection and examination method with which the remaining endurance strength of endodontic files can be inspected non-destructively and equipment for conducting such inspection; said endodontic files are mainly manufactured from stainless steel or superelastic TiNi alloy for purpose of cleaning the diseased portion of root canals.

2. Description of the Prior Art;

The occlusal surface of tooth is formed with coronal body made of hard enamel structure, under which the dentine structure is found. Beneath the dentine structure, there is a pulp chamber and it extends to a root canal toward the root apex. If the dental decay was developed, the caries is initiated by the attack on the enamel surface. Later on, the dental caries will proceed to attack the root canal. The root canal therapy may be defined as the complete removal of the irreversibly damaged dental pulp followed by cleaning, shaping and filling of the root canal system so that the tooth may remain as a functional unit in the dental arch.

Certain principles must be adhered to during the preparation of all root canals; (1) always maintain the original preoperative shape of the root canal and work within the confines of that canal, (2) produce a continuously tapering three-dimension which has its narrowed cross-sectional diameter at the apical constriction, (3) create sufficient width in the canal to permit the use of irrigation in the removal of organic debris and bacteria from the entire canal and to allow adequate space for condensation of the solid-core root canal filling material such as Gutta-percha.

Files are the most useful instruments in the endodontics for a purpose of the removal of hard tissue in canal enlargement. They are manufactured by twisting a blank, which is a square (or sometimes triangle) rod, producing a series of cutting flutes. Mechanical or engine-powered instrumentation has developed into the sonic and ultrasonic fields with a reduction in preparation time. What has improved is the irrigation and concurrent removal of toxic debris from the root canal.

An endodontic file has normally two functions; they are filing action and reaming action. If the filing action is used, the flutes scrape against the walls, gouging a portion of dentin and removing it from the canal. If reaming action is used, clockwise turning should be employed. The flutes contacting the walls scrape and shave the dentine to widen the preparation.

Due to complexity and irregularity of root canal morphology, the filing action and reaming action make the complete endodontic therapy more complicated and challenging. In order to accommodate to such complicated and irregularly shaped root canals, the endodontic file should be very elastic, particularly the tip portion thereof. Furthermore, there is a variety of size in terms of tip diameter and stem diameter, and length as well.

Recently, TiNi material has been extensively used to fabricate the endodontic files because these alloys possess unique characteristics of superelasticity. Superelastic property reduces the chance for procedural accidents such as zipping, ledging and transportation of files. While the superelastic properties of TiNi instruments are highly desirable, instrument breakage within the canal can still occur. It is said that if the endodontic file was broken and left in the portion of the root canal, it is not the malpractice. But, if the endodontist fails to record this evidence on the patient's chart and fails to mention this incidence to his or her patient, it is the malpractice.

M. L. Zuolo et al. observed that the endodontic files were failed due to various mechanical reasons; they may include a rapid wear, breakage, gouges and pits on flutes, and twisting on shaft [Journal of Endodontics, Vol. 18, p.336; 1992]. Moreover, J. P. Druett et al. investigated the low cycle fatigue damage process on superelastic TiNi endodontic files [Journal of Endodontics, Vol. 23, p. 77; 1997]. They found that all tested TiNi files were fatigue-failed and number of cycles to failure depended on the curvature angle (which indicates how sharp the root apex is turned and shaped).

If the file is evaluated to be non-damaged, it will be sterilized and re-used (or recycled) to the next patient. The normally practiced sterilization is an autoclave-sterilization at 120° C. for 30 minutes at 20 psi pressure. B. F. Mitchell found that the stainless steel files have shown a decrease in fracture resistance following repeated autoclave sterilization [Oral Surgery, Vol. 55, p.204; 1983]. On the contrary, E. P. Kiss et al. observed that regardless of the size of TiNi rotary files, multiple (five) cycles of autoclave sterilization resulted in a significant increase in torsional fracture resistance [Journal Dental Research, Abstract 547; 1997]. However, Y. Oshida observed that the progressive damage on TiNi files was found to be dominant over the recovery process by the autoclaving (if any) [unpublished data; 1998].

As described in the above, although the breakage and leaving the portion of endodontic file in the root canal is not malpractice, it will cause many problems to certain types of patients. If the patient is hypersensitive to nickel element, he or she will be suffering from the nickel allergic reaction. For a more serious case, the dissolved nickel element will act as a carcinogenicity. Because nickel content in the TiNi (about 50 weight %) files is higher than that in stainless steel (about 8 weight %) files, the above potential problems will be worsened when the superelastic TiNi files are broken and left behind the root canal portion. Although the biocompatibility of TiNi implant was well documented, it is based on the in vitro studies using the artificial saliva, which has a chlorine concentration with about seven (7) times dilute than that of dentinal liquid. Accordingly, it can be easily speculated that the dissolution of nickel element out of the broken TiNi would be much higher than the case in the intraoral environment.

Even with these potentially harmful element containing materials, there is no scientific standards to assess the cumulative damage on TiNi or stainless steel files before the mechanical breakage. What is normally practiced with the endodontics is that the degree of bending of the tip portion of files and cutting efficiency of used files are major two parameters for the endodontist to evaluate the progressive damage and judge as to whether or not it can be recycled after the autoclave-sterilization or should be abandoned. These observation is normally performed by either naked eyes or under relatively low magnification lens (for example, x20). Hence these are the macroscopic inspection and limited only on the surface layers.

In light of this background, there remain needs for novel endodontic file inspection method that are more reliable to an endodontist and safe to the endodontic patient and for fabricating the equipment for performing these novel inspection on endodontic files. The present invention addresses these needs.

SUMMARY OF THE INVENTION

The present invention was developed in order to overcome aforementioned drawbacks associated with the currently practices done by the endodontist. It is, therefore, an objective of the present invention to provide a novel inspection method to monitor the cumulative damage and to determine that the endodontic file has reached its endurance limit, and an equipment with which these inspection can preform non-destructively on endodontic files.

In order to achieve the objective, accordingly, the first preferred embodiment of the present invention provides an inspection method for the endodontic files in order to assess the cumulative damage of the files employed for the cleaning the diseased portion of the root canals. The inspection method comprises various processes; including a data measuring process in order to measure the data regarding to the electric resistance of the endodontic files, a judging process in order to compare the measured data obtained through the previous process to those threshold critical strength data which were obtained in advance, and to judge as to whether or not the file has been damaged to the critical level, and an alarming process in order to issue the warning whenever the previous process indicates that the file has been reached to its critical level of the cumulative damage, so that it should be discarded or annealed to set the damaged file out of service condition.

According to the preferred embodiments of the inspection method of the present invention, when the file is judged to reach its critical level of the damage during the judging process, said judging process furthermore includes a setting process for the un-usable condition on the file, so that the file can not and should not be used any more.

According to the second preferred embodiment of the present invention provides an equipment to perform the inspection as mentioned above. The equipment comprises a file sample holding means in order to hold the endodontic file to be inspected, the data input means in order to input the data obtained from the file sample, the electric resistance data measuring means in order to measure the electric resistance from the file sample to be inspected, memory means of the inspected information in order to store the data on the electric resistance measured from the file sample, a judging means in order to make an judge as to whether or not the file sample has been damaged and reached to its critical strength level of cumulative damage, being based on data with regard to the resistance values measured from the aforementioned resistance data measuring means and resistance value data of the critical strength corresponding to the data on the file sample which is read out from said inspection information memory means, and an alarming means to issue an alarm when the file sample reaches its critical strength level of the cumulative damage.

The inspection equipment according to the present invention is furthermore characterized by that it contains a holding body in order to hold a plurality of files forming one complete set of files and a kit case which is provided by the holding body.

The inspection equipment of the present invention is moreover characterized by that the data on aforementioned resistance value is the resistance value of said endodontic files which are measured by the resistance data measuring means.

Furthermore, the inspection equipment according to the present invention is characterized by that the data on aforementioned resistance value is the percentage changes in resistance obtained from the file sample measured by the above mentioned resistance data measuring means.

The inspection equipment according to the present invention is still furthermore characterized by that the equipment is provided by an elastic bending deformation means in order to apply the elastic bending deformation on the file sample when measuring the resistance data. The reason for limitation on "elastic" bending deformation is based on the fact that if metal is bent plastically, the internal disorder of crystalline structure takes place, resulting in increasing the electric resistance. However, during the measuring the resistance, if the file sample is elastically bent, then the contact points are more tight, so that the accuracy of measuring the resistance will be improved.

Moreover, the inspection equipment according to the present invention is characterized by that the equipment is provided with a setting means for un-usable condition of files in order to set the file sample to be un-usable condition when issuing the alarm.

These and other objects, characteristics, and advantages of the present invention will be apparent upon reviewing the descriptions herein.

DETAILED DESCRIPTION OF PREFERRED EMBODIMENTS

In the following, the present invention will be described in a great detail by referring to drawings.

Figure 1:
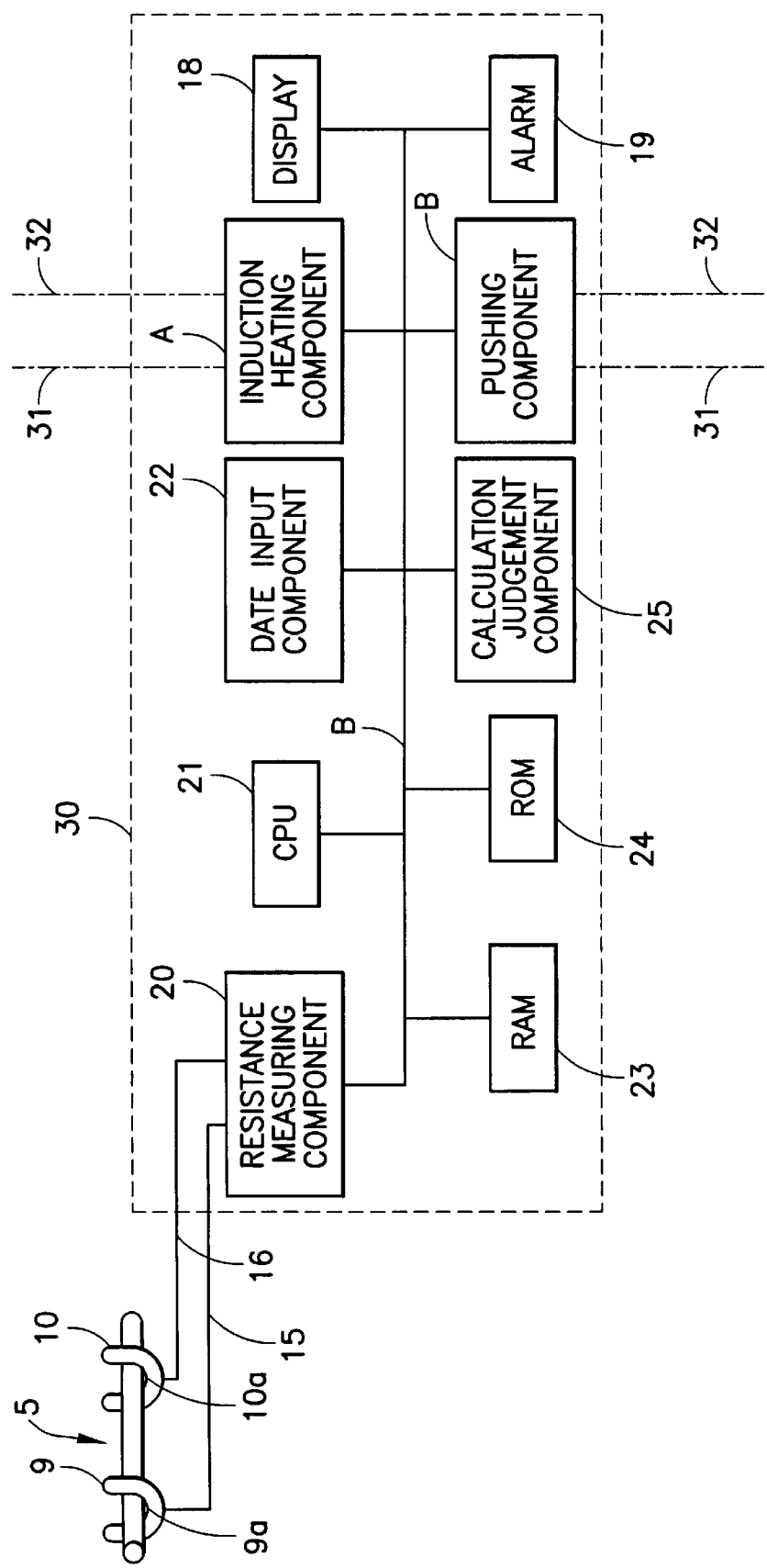
FIG. 1 provides a block diagram of one example of the embodiment according to the present invention.

Referring now specifically to FIG. 1, illustrated is a preferred design of providing a file sample holding body 5 comprising holding pieces 9, 10. To holding pieces 9, 10, connected are an end portion of endodontic files and inspection electrodes 9a, 10a, respectively. On the other hand, an inspection unit 30 is connected to inspection electrodes 9a, 10a through the lead wires 15, 16.

Furthermore, to the side wall portion of a kit case 1, an induction heating component A is installed. The induction heating component A has a unique function to anneal the tip portion of the endodontic file which was inspected and evaluated to be no more useful because the file has reached its critical level of strength due to the cumulative damage. The annealed file loses its cutting capability the root canal. Means for setting the damaged files into an un-usable condition is not limited to an annealing the file to make it weak and soft, but also the tip portion of the damaged file can be cut off. Alternatively, it may be plastically bent using the aforementioned bending deformation means if the applied force is controlled, so that it is obvious to see that it has a shape of an un-usable. The position for installing the induction heating component A is corresponded to the tip portion of files which are set at the file sample holding body 5.

Moreover, a pushing component B is provided on the lid 2. The pushing component B is positioned with correspondence to the tip portion of the file sample to be inspected (which is held on the file sample holding body 5), and has a function to provide a bending deformation to the endodontic files during the inspection.

With the inspection unit 30, CPU 21 which controls the overall operations is connected to lead wires 15, 16 to an input terminal through the busbar B, and is furthermore connected to a resistance measuring portion 20 to measure the electric resistance of the endodontic files. To the CPU 21, a data input portion 22 which inputs data information with regard to size and type of material of files is connected through the busbar B. Furthermore, a display 18 is also connected to the CPU 21 through the busbar B. The display 18 has a displaying function of various data generated during the performing the inspection.

Similarly, ROM 24 and RAM 23 are also connected to the CPU 21 through the busbar B. The ROM 24 stores all control programs which are required to perform the appropriate inspection. The RAM 23 stores the resistance data of the threshold critical strength of endodontic files with correspondence to the data on size and the type of material of file samples to be inspected. Various data generated during the inspection are also written in the RAM 23.

Furthermore, a calculation judgement component 25 and an alarm 19 are connected to the CPU 21 through the busbar B. The calculation judgement component 25 can judge as to whether the endodontic file under inspection has reached its critical strength level of cumulative damage, based on the resistance value measured by the resistance measuring component 20 and the resistance data on the critical strength which are read-out with correspondence to the inspection data from the RAM 23. When the strength of the endodontic file under the inspection is judged to reach its critical level of the pre-determined allowable strength, the alarm 19 starts to issue an alarm.

With regard to the annealing means by using an induction heating source as described previously, the required means to make the file, which is evaluated to reach its critical limit of cumulative damage, un-usable is not only limited to the induction heating component A, but also other types of means be employed, as described before. The induction heating component A can be used also as a holding the file sample as the file sample holding body 5 does, but the induction heating component A can also be provided on the different location within the inspection unit 30. Furthermore, as an other embodiment, the induction heating component can be installed not in the inspection unit 30, but in the separate unit (not shown). Pushing component B can be controlled in order to load the applied force form the elastic to plastic deformation, so that the damaged file can be set into an un-usable condition. Similarly, the cutting means (not shown) can be employed in order to achieve the same purposes.

The induction heating component A and the pushing component B are connected to the CPU 21 through the busbar B. The induction heating component A is provided to the area close to the tip portion of the file sample to be inspected and connected to the lead wires 31, 32 with which the file sample that is judged to be un-usable is ready to be annealed so that the endodontic file already damaged with beyond its critical level can not be re-used or recycled. The pushing component B is connected also to the lead wires 31, 32 to apply the elastic bending deformation positioned at area in the vicinity of the tip portion of the file sample.

Figure 3:
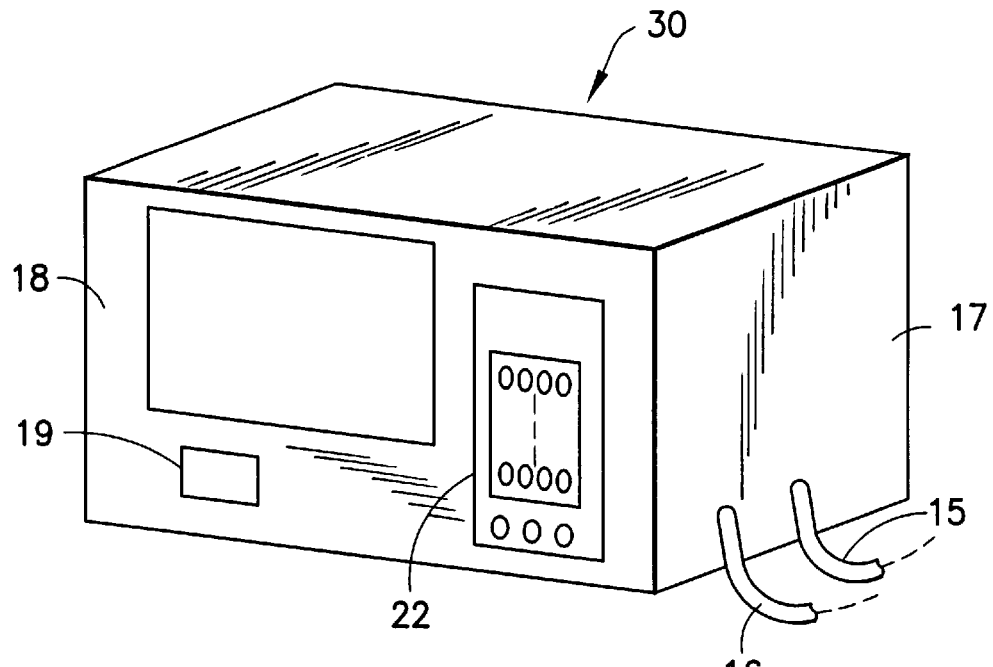
FIG. 3 provides a perspective view of an inspection unit of FIG. 1.

The inspection unit 30, according to the present invention, is stored in the rectangular-shaped case 17, as seen in FIG. 3. The display 18 is situated at about the center portion of the front panel thereof. On one side of the front panel, the data input portion 22 is provided and an alarm 19 is placed at lower portion below the display 18.

Figure 2:
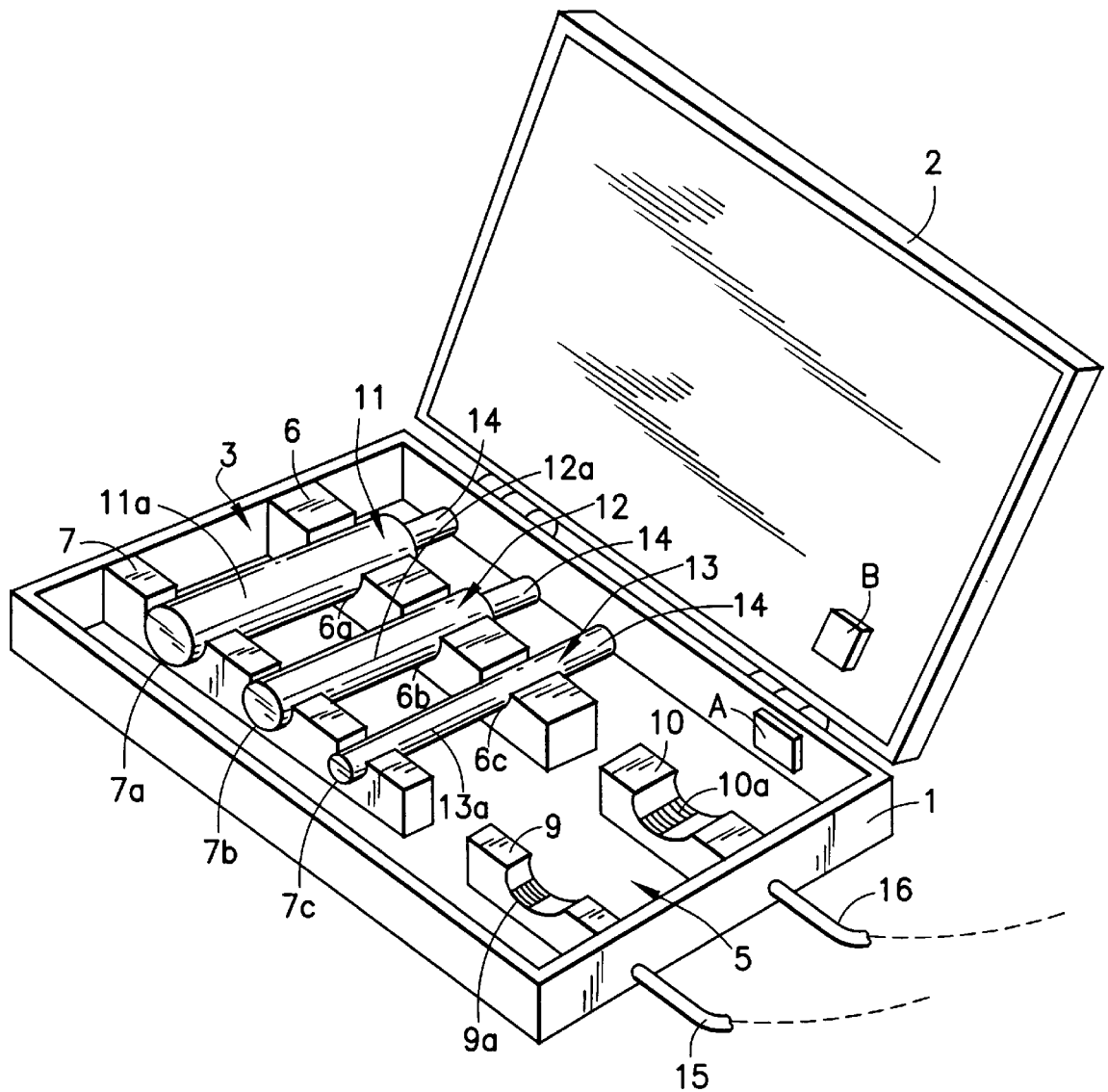
FIG. 2 provides a perspective view of a kit case of FIG. 1.

According to the present invention, as seen in FIG. 2, a large size endodontic file 11, a medium size endodontic file 12, a small size endodontic file 13 are placed together as a set in a kit case 1. These endodontic files 11,12,13 are held at the holding pieces 6,7 which are provided at the bottom plate of the kit case 1. Furthermore, at one end portion of the bottom plate of the kit case 1, the file sample holding body 5 is provided which consists of holding pieces 9,10 to which the electrodes 9a, 10a are firmly adhered respectively. The file sample holding body 5 is able to hold all possible sizes of files such as files 11,12,13 and is structured in such a way that both ends of file portions of the endodontic files can be in contact to respective electrodes 9a, 10a.

While the kit case 1 is closed with the lid 2 when endodontic files 11,12,13 are stored, the lid can be opened during the endodontic practice and an appropriately selected file (11, 12, or 13) can be placed at the file sample holding body 5 so that the file which is just about to use on the patient does not yet reach its critical level of strength by cumulative damage.

Figure 4:
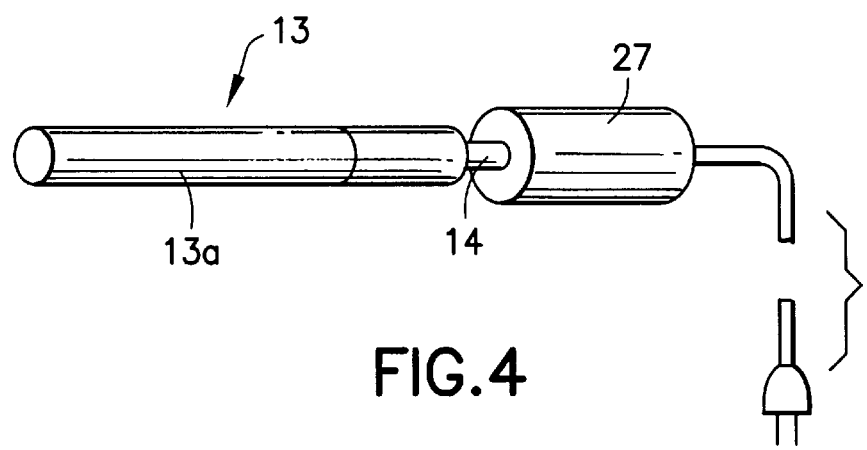
FIG. 4 provides a structural view of an endodontic file of FIG. 1.

Moreover, respective file portion 11a,12a,13a are formed at the endodontic files 11,12 13. A chucking bar 14, which is common size to all different sizes of files, is provided at the other end side from the file portion of the endodontic files 11,12 13. Upon the endodontic therapy, as seen in FIG. 4, the selected file, for example file 13, is attached to a motor 27 through a common chucking bar 14, so that the file 13 can rotate at a high speed through the motor 27 in order to clean the diseased portion of the root canal. As an alternative way for using the endodontic files, the selected file can be attached to a turning handle which can manually be operated by an endodontist (not shown).

For purposes of promoting a further understanding of the present invention, including its various aspects and advantages, the following structural and operational Examples are provided. It will be understood that these Examples are illustrative, and not limited, of the present invention.

As one clinical example for the endodontic therapy, an endodontist chooses one appropriate size of file out of the file set (11, 12, 13) according to the morphological data on the specific tooth of the patient which can be obtained radiographically. For example, if the endodontist chooses the file 13 which has 0.3 mm diameter at the tip portion thereof, 1.0 mm diameter at the base portion and 30 mm of length, the file 13 is set and held at the file sample holding body 5 of the kit case 1.

Following the setting the file 13 at the file sample holding body 5, the operator (who can be an endodontist or a dental assistant) operates the data input portion 22 to input the electric conductivity, k, of the type of material of the selected endodontic file 13, cross-sectional area, Sc, and length, L, thereof and operates the start button to start the equipment.

In a case when the electric resistance is measured and inspected while applying the elastic bending deformation to the endodontic file, the data input portion 22 is operated, data on the pushing inspection is input, the start button is operated to start the equipment with keeping the lid closed.

With the above conditions, the electric resistance of the file portion 13a of the endodontic file 13 is measured through the resistance measuring portion 20 which both ends of file portion 13a of the file 13 are connected through lead wires 15,16. This measurement is achieved upon the command from CPU 21 and measured data is stored at RAM 23.

In general, during performing the endodontic cleaning on the root canal, the endodontic file 11,12,13 is subjected to a complicated external force, which could cause the file twist, bend, stretch, or wear. In many cases, the flute portion will be unwound to show a partial elongation. All these plastic deformation will deteriorate the original mechanical properties of the endodontic files, including static tensile strength, elasticity, fatigue strength. If any one of these damages process or any combination of these causes the internal disorder of the material integrity, the material will simply fracture. The fracture can include a tensile breakage,. a bending rupture, or the fatigue failure. It is well documented that these failures never take place upon one loading like a brittle catastrophic failure, but they occur after a certain period of time, which is characterized by the fact that these failures are due to the cumulative damage. If the cumulative damage—internal disorder in the metallic crystalline structures—reaches its critical level, then the material starts to fail. These progressive damage processes are irreversible. If the endodontic file is experiencing one of these cumulative damage processes, it will suffer from either stretching, bending, or simply fatigue failure. By any one of these irreversible deformation, the file is not any more functioning of a filing action or a reaming action.

Figure 5:
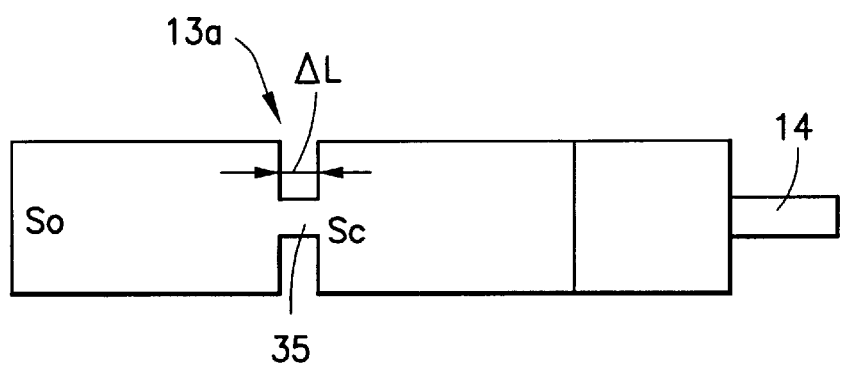
FIG. 5 provides a view explaining a relationship between the endurance limit and resistance value of the endodontic file.

In more details, if during the damage process of the endodontic file 13, the file portion 13a is twisted, bent or worn off partially, the narrow zone 35 will be formed, as illustrated in FIG. 5. Assuming that the rest of the portion, except the narrow zone 35, of the file is unchanged dimensionally, the resistance, R, of the total portion of the file 13a can be summation of Rc (resistance of the narrow zone 35) and Ro (resistance of the file except narrow zone 35). Let $\Delta L$ be the length of the narrow zone 35, Sc be the cross-sectional area of the narrow zone 35, So be the cross-sectional area of file portion 13a, L be the length of file portion 13a, and k be the electric conductivity of the file portion 13a; the total resistance, R, of the file 13a can be given by the following equation (1).

$$R = Ro + Rc = Ro + 1/k\{(1-\Delta L)/So + \Delta L/Sc\} = Ro + \Delta L/k(1/Sc - 1/So) \quad (1)$$

As been clearly understood from the above equation (1), once the narrow zone 35 is formed in the file portion 13a of the endodontic file 13, the resistance value of the file portion 13a increases in proportional to the length $\Delta L$ of the narrow zone and in reversely proportional to the cross-sectional area Sc thereof. The changes in resistance value is not only due to the dimensional changes, as described in the above, but also to the internally disordered crystalline structures, which is known as dislocations. Hence, the remarkable changes in electric resistance can be observed from the stage which is even before the dimensional changes such as an occurrence of the narrow zone 35 can be observed.

According to the present invention, the critical values of resistance corresponding to the electric conductivity, k, based on the type of the material for files 11, 12,13, cross-sectional area, Sc, based on their sizes, and the length, L, are previously measured and all necessary reference data are stored in the RAM 23.

When the measured data done by the resistance measuring portion 20 is stored in the RAM 23, the resistance value for the critical strength corresponding to the electric conductivity, k, cross-sectional area, Sc, and length, L, of the file 13 and measured data of the resistance done by the resistance measuring portion 20 on the file 13 are read-out from the RAM 23 by a command from the CPU 21; then the measured resistance value of the file 13 judges if the file's resistance reaches the critical level of strength or not by the calculating judgement portion 25 which is operated under the command of CPU 21.

If the calculation judgement portion 25 judges that the measured resistance value on the file 13 is within the dangerous zone which is previously determined with respect to the critical level of strength of the cumulative damage, the CPU 21 commands the alarm 19 to issue an alarm sound, and, at the same time, a message "Since this endodontic file has already reached its critical strength, please don't use it." is displayed on the display 18.

At the next step, the tip portion of the file 13 is annealed by the induction heating component A, so that the damaged file is out of service. In an alternative way, the tip portion can be cut off or plastically permanent-bent.

In the above case, the remaining life of the endodontic file can be estimated, based on the measured resistance (which relates directly to the extent of damage), and can be displayed on the display 18. If the data regarding the changing rate of resistance is written-in, the accuracy of estimating the remaining life can be improved.

On the other hand, if the calculation judgement portion 25 judges that the measured resistance of the endodontic file is out of the dangerous zone which is already determined by the electric resistance with respect to the critical strength, the CPU 21 commands the display 18 to send and display the message "This endodontic file is (re)-usable."

According to the present invention, after the endodontist or the dental assistant sets the endodontic file, which is appropriately chosen from the file sets 11,12,13 being stored in the kit case 1, to the file sample holding body 5 of the kit case 1 and inputs data with regard to the endodontic file from the data input portion 22; the resistance of the file portion measured by the resistance measuring portion 20 and the resistance for the critical strength with correspondence to the data on file read-out from the RAM 23 are brought together and compared by the inspection unit 30. Then if the calculation judgement portion 25 judges that the file has already reached its critical strength, the alarm starts to sound, so that the endodontist or the assistant knows that the file is not useful any more. As a result, a more safe and reliable endodontic therapy can be practiced than the conventional way of evaluating on the extent of the damage on files. Moreover, with the above novel way for the inspecting the damaged file, any nickel-related risks (including an allergic reaction or cancer, as described previously) can be eliminated.

In the aforementioned embodiment, the endodontic file, which was judged to reach its critical strength and is discarded, is going to be annealed so, that the tip portion is now out of function. The embodiment of the present invention is not restricted to the above, but the tip portion of the endodontic file (which already reached its critical strength) can also be broken or bent permanently, so that it can not be used or recycled any more.

In the above explained embodiments, the judgement on the strength has been described based on the resistance value measured on the endodontic file, but the strength can be judged based on the changing rates in resistance of the endodontic files, too.

Furthermore, according to the present invention, the data on the file sample to be inspected are input with respect to the electric conductivity, k, cross-sectional area, Sc, and length, L, from the data input portion, however, data on pattern, which is previously determined on the endodontic file, can be input through a bar-cord or the like. By either means of inputting data, if the file was judged to be discarded and the file was destroyed, all data and/or bar-cord should be removed from the memory. The bar-cord is assigned to each individual endodontic file in order to identify the file itself, size, dimension, type of material and most importantly progressive damage until the moment that it is assessed to reach its critical strength level. Since none of the currently marketed endodontic files has any type of the bar-cord, the putting the identification bar-cord on the endodontic file will be the first thing to do.

Moreover, according to the present invention, since the file sample holding body 5 which can hold a plurality of endodontic files as a set and a kit case having file holding pieces are provided, while the endodontic file inside the kit case is held by the file sample holding means inside the kit case, a quick and simple inspection on the endodontic file can be achieved.

While this invention has been explained in detail in the foregoing description, it will be understood that the present invention is not limited to the specific embodiments disclosed. Rather, many modifications and variations will be apparent to those of skill in the art and may be practiced without departing from the spirit and scope of the present invention. For example, in accordance with the invention, the changes in length of the file portion of the endodontic file can also be used as a cumulative damage indicator. Again, original length of each file before an usage should be input. Data on length changes can corporate with the internal changes in terms of resistance changes, so that by continuously monitoring the length of the file portion, the critical level of strength of cumulative change can also be determined.

What is claimed is:

1. An inspection method for inspecting an endurance strength of an endodontic file used for cleaning the diseased portion of the root canal comprising a data measuring process to measure the data with regard to the electric resistance of the endodontic file;

a judgement process to compare the data measured by the data measuring process to critical strength data which is previously measured and to make a judgement as to if the file reaches its critical strength level of cumulative damage; and an alarming process to issue an alarm if the file is judged to reach its critical strength.

2. The inspection method for the endodontic file cited in claim 1 which furthermore includes a setting process to set the file to be an un-usable condition which said file is judged to its critical strength by the judging process.

3. An inspecting equipment to inspect the endurance strength of the endodontic file for cleaning the diseased portion of the root canal comprising a file sample holding means to set the file to be inspected;

a data input means to input the data on file to be inspected being held at the file sample holding means;

a resistance measuring means to measure the electric resistance on the file to be examined;

a memory means for inspection information to store the resistance data on the critical strength with correspondence to the data on endodontic file;

a judging means to make a judgment as to if the file reaches its critical strength, based on data regarding the resistance value measured by the resistance measuring means and resistance value data on the critical strength with correspondence to data of the endodontic file which is read-out from the memory means for inspection information; and an alarming means to issue an alarm when the file is judged to reach its critical strength.

4. The inspection equipment for endodontic file cited in claim 3, which is furthermore provided with a kit case having a file sample holding body to hold a plurality of endodontic files and the file sample holding means.

5. The inspection equipment for endodontic file cited in claim 3, in which data about the resistance value is the resistance data of the endodontic files measured by the resistance data measuring means.

6. The inspection equipment for endodontic file cited in claim 3, whereby data about the resistance value is the change rates in resistance of endodontic files measured by the resistance data measuring means.

7. The inspection equipment for endodontic files cited in claim 3, whereby an applying means of elastic bending deformation to the endodontic file to be examined when measuring the resistance by the resistance data measuring means; while said applying means can be used in order to bent plastically with a permanent deformation the damaged endodontic file for a purpose of setting the damaged file into an un-usable condition.

8. The inspection equipment for endodontic files cited in claim 3, whereby a setting means is furthermore provided to set the endodontic files to be an un-usable condition while the alarming means issuing an alarm sound.

* * * * *